(12) United States Patent
Wijay et al.

(10) Patent No.: US 9,597,223 B2
(45) Date of Patent: Mar. 21, 2017

(54) REVERSIBLE ACUTE OCCLUSION IMPLANT, DELIVERY CATHETER AND METHOD

(76) Inventors: Nandhika Wijay, Friendswood, TX (US); Bandula Wijay, Friendswood, TX (US)

(*) Notice: Subject to any disclaimer, the term of this patent is extended or adjusted under 35 U.S.C. 154(b) by 236 days.

(21) Appl. No.: 13/566,080

(22) Filed: Aug. 3, 2012

(65) Prior Publication Data

US 2013/0312762 A1 Nov. 28, 2013

Related U.S. Application Data

(63) Continuation-in-part of application No. 13/478,880, filed on May 23, 2012.

(51) Int. Cl.
*A61F 6/22* (2006.01)

(52) U.S. Cl.
CPC .................................. *A61F 6/225* (2013.01)

(58) Field of Classification Search
CPC ...... A61B 17/0057; A61B 2017/00654; A61B 17/12; A61B 17/12022; A61B 17/1204; A61B 17/12031; A61B 17/12036; A61B 17/12099; A61B 17/1214; A61B 19/54; A61B 2019/5425; A61B 17/42; A61B 17/82; A61F 2/02; A61F 2002/018; A61F 2/04; A61F 6/14; A61F 6/142; A61F 6/146; A61F 6/18; A61F 6/20; A61F 6/208; A61F 6/24; A61F 6/22; A61F 6/225; A61F 6/206
USPC ................. 128/830–833, 839–840, 842–843
See application file for complete search history.

(56) References Cited

U.S. PATENT DOCUMENTS

| | | | | |
|---|---|---|---|---|
| 4,043,338 A | * | 8/1977 | Homm | A61M 31/00 604/105 |
| 4,246,896 A | * | 1/1981 | Horne, Jr. | A61F 6/14 128/833 |
| 4,874,139 A | * | 10/1989 | Kewin | B65H 75/187 242/118.31 |
| 5,287,852 A | * | 2/1994 | Arkinstall | A61M 16/0465 128/200.24 |
| 5,601,600 A | | 2/1997 | Ton | |
| 5,746,769 A | | 5/1998 | Ton et al. | |
| 5,861,043 A | * | 1/1999 | Carn | A61F 2/4614 606/62 |
| 5,893,850 A | * | 4/1999 | Cachia | A61B 17/683 606/326 |
| 5,935,137 A | | 8/1999 | Saadat et al. | |
| 5,935,169 A | * | 8/1999 | Chan | A61F 2/0095 411/55 |
| 6,251,141 B1 | * | 6/2001 | Pierson, III | A61F 2/30723 606/95 |
| 6,357,443 B1 | | 3/2002 | Loy | |
| 6,629,533 B1 | * | 10/2003 | Webb | A61B 17/12022 128/887 |
| 7,749,279 B2 | * | 7/2010 | Twomey | A61F 2/30723 623/23.48 |
| 7,846,160 B2 | | 12/2010 | Payne et al. | |
| 8,100,129 B2 | * | 1/2012 | Swann | 128/831 |
| 8,443,808 B2 | * | 5/2013 | Brenzel et al. | 128/831 |

(Continued)

*Primary Examiner* — Ophelia A Hawthorne
(74) *Attorney, Agent, or Firm* — Steve Rosenblatt

(57) ABSTRACT

A permanent reversible acute occlusion implantable device and method are described for immediate occlusion of a body lumen, such as the fallopian tubes of the human female, but which can be reopened when necessary at a later date.

29 Claims, 10 Drawing Sheets

(56) References Cited

U.S. PATENT DOCUMENTS

| | | | |
|---|---|---|---|
| 8,747,430 B2* | 6/2014 | Porter | A61B 17/12022 606/200 |
| 2003/0066533 A1* | 4/2003 | Loy | A61B 17/12099 128/831 |
| 2008/0135054 A1* | 6/2008 | Callister et al. | 128/831 |
| 2009/0054723 A1* | 2/2009 | Khairkhahan | A61B 17/0057 600/16 |
| 2010/0234878 A1* | 9/2010 | Hruska | A61B 17/0057 606/213 |
| 2014/0163608 A1* | 6/2014 | Osypka | A61B 17/0057 606/213 |

\* cited by examiner

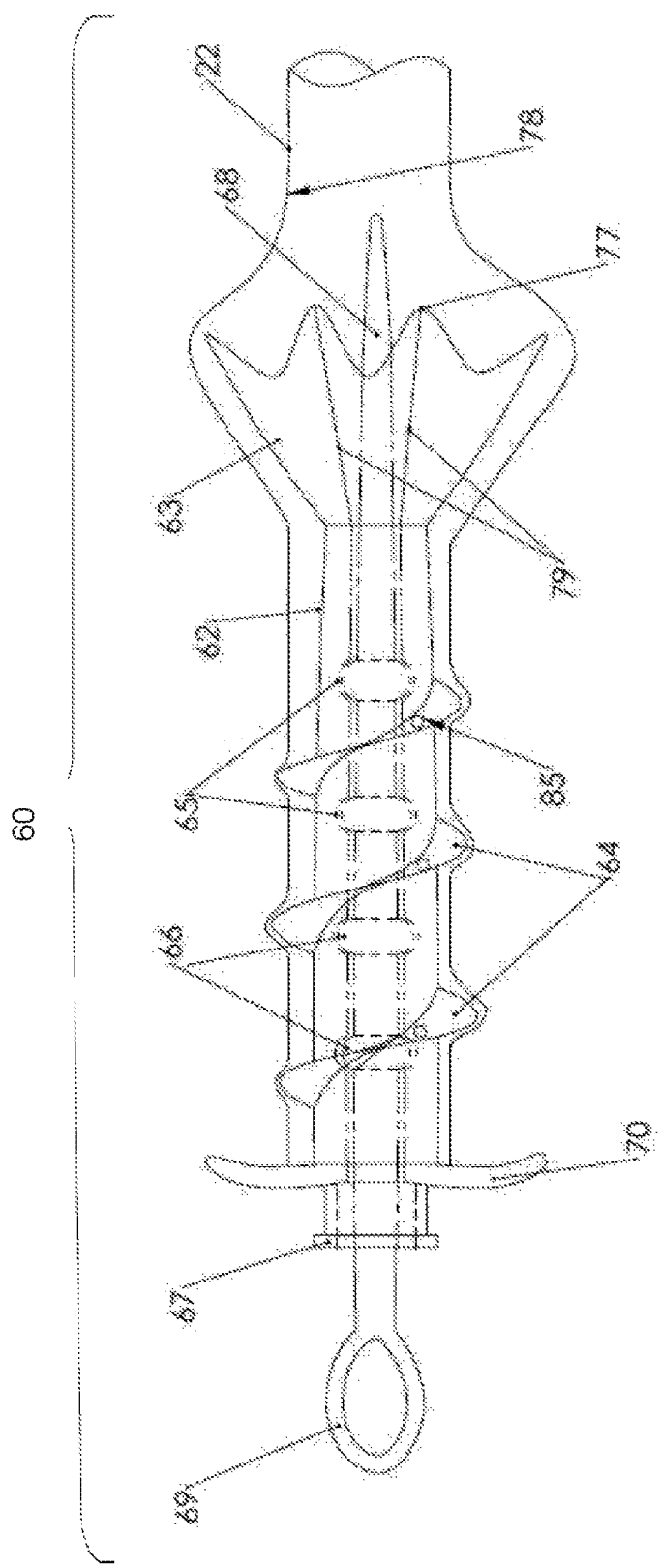

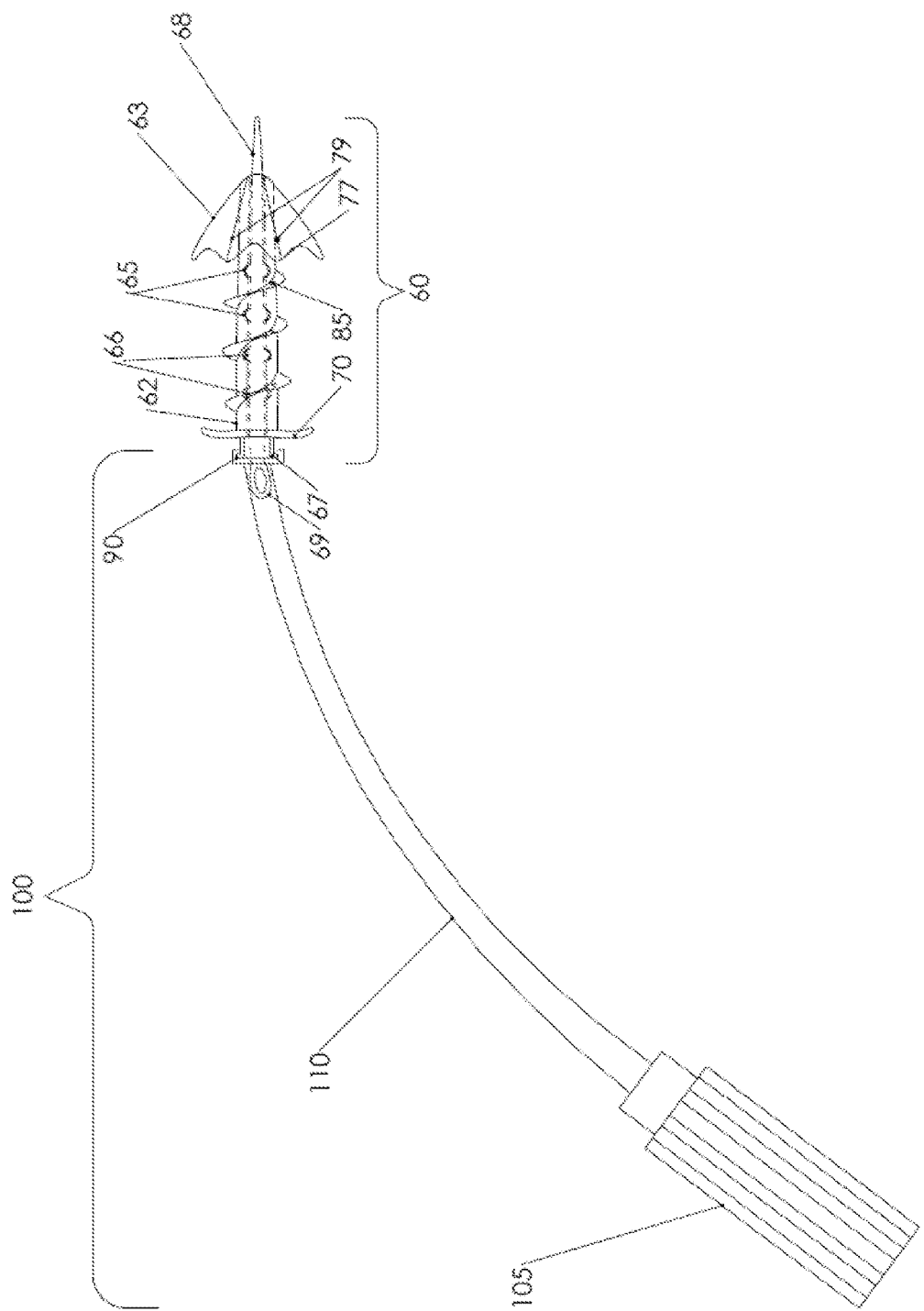

REVERSIBLE ACUTE OCCLUSION IMPLANT, DELIVERY CATHETER AND METHOD

CROSS REFERENCE TO RELATED APPLICATION

This application is a continuation-in-part of U.S. patent application Ser. No. 13/478,880, filed on Jul. 11, 2007, and claims the benefit of priority from the aforementioned application.

FIELD OF THE INVENTION

The present invention relates to a reversible endo-luminal occluding device, which when implanted within the fallopian tubes, facilitates female sterilization, but which can be reversed, anytime after deployment, if the patient decides to bear children.

BACKGROUND OF THE INVENTION

Female sterilization is a very common practice and is performed frequently throughout the world. Traditionally, the most common female sterilization method is fallopian tube ligation, a procedure that utilizes a trans-abdominal approach for the occlusion, or tying, of the fallopian tubes. Despite its worldwide use, tubal ligation via the trans-abdominal approach is associated with substantial trauma, discomfort, hospital stays, and complications, such as bleeding, infection, reactions to general anesthetic, and bowel perforation. The trans-abdominal approach involves surgery, is difficult to reverse, and is not readily available to many women throughout the world. Even though local anesthetic is considered an option for the trans-abdominal approach to tubal ligation, almost all of these sterilization procedures are performed under general or spinal anesthesia. In addition, the trans-abdominal approach to tubal ligation requires incisions that invade the peritoneal cavity, thereby raising the risk of injury to intra-abdominal structures.

In order to avoid the problems associated with trans-abdominal tubal ligation procedures, various trans-cervical approaches to tubal sterilization have been proposed. The trans-cervical approach to sterilization involves the insertion of a catheter or sterilization device directly into the fallopian tubes via the reproductive tract, eliminating the need for general anesthetic and abdominal incisions. Initial trans-cervical approaches to tubal sterilization involved radiofrequency, chemical or heat induced scarring, or liquid silicone injections. However, these approaches have all failed due to safety and efficacy concerns. Chemical scarring agents, such as quinacrine, iodine, and methylcyanoacrylate, require repeated applications and have problems concerning bio-compatibility. Thermal blocking procedures, which induce the formation of scar tissue within the fallopian tubes, have high failure rates and major complications such as uterine bleeding and bowel perforation. Electrocautery methods, which employ an electric current to induce scar tissue within the fallopian tubes, are also unsatisfactory because they do nor scar a sufficient amount of tissue and because they can burn surrounding organs, particularly the bowel.

Current trans-cervical methods involve occluding the fallopian tubes by implanting a small occluding device. The occluding devices in the prior art are usually in the form of a cylindrical plug or a coil. For instance, Loy in U.S. Pat. No. 6,357,443 describes a removable fallopian tube plug consisting of a tubular (cylindrical) elongate member with a number of fingerlike protrusions that extend radially outwards creating a barrier and thereby occluding the fallopian tubes. Additionally, Saadat et al. in U.S. Pat. No. 5,935,137 describe a fallopian tube occluding device for female sterilization which is a plastic, rubber, or metal elongate hollow tubular (cylindrical) structure with ribs that are either coated with copper or are interlaced with copper rings. The hollow portion of this device has a valve, or seals with a hydrogel, after the device is implanted into the fallopian tubes.

Coils, which have a helical outer surface and which assume a bent shape when released from the delivery catheter system, are also used to occlude the fallopian tubes. For example, Ton et al. in U.S. Pat. Nos. 5,601,600 and 5,746,769 describe the use of a coil to occlude the fallopian tubes. The device consists of polyethylene terephthalate (PET) fibers wrapped around a stainless steel core that is surrounded by 24 or more coils of nickel-titanium alloy. After the device is deployed within the fallopian tubes, the PET fibers induce the tubal epithelium to undergo fibrosis, which results in tubal occlusion. The device also relaxes to its natural bent shape once it is deployed in the fallopian tube. The tubal occlusion process from these devices takes about three months to complete and must be confirmed via a hysterosalpingogram.

U.S. Pat. No. 7,846,160 teaches the use of an exterior screw thread to advance a lumen plug by rotation In FIG. 3. In FIG. 4 barbs are held under a sheath such that when the sheath is retracted, the barbs spring out and point proximally to prevent removal.

Most of these devices eventually become dislodged or have found to be only moderately effective in preventing pregnancy. In addition, all of the fallopian tube occluding devices are either composed of metal or have metal components. As a result, various surgical procedures involving electrosurgery, radiofrequency, or microwave energy cannot be performed near the implants. Therefore, a need exists for a female contraceptive device that does not contain any metal, does not migrate once implanted, and which provides immediate protection against conception. The occlusion device of the present invention fulfills these needs.

SUMMARY OF THE INVENTION

The present invention consists of a permanent reversible acute occlusion implantable device and method for immediate occlusion of a body lumen, such as the fallopian tubes of the human female, but which can be reopened when necessary at a later date. The implant, an acute occlusion device, consists of a small narrow tube, which is closed with the use of a plug made of an elastomer such as silicone rubber, and which carries a conical-shaped structure that is located near the distal end of the small narrow tube, which can function as an occlusion means for the body lumen. The small narrow tube of the implant has screw threads or, alternatively, serrations which embed into the wall of a body lumen, and which may be utilized to advance, and seal, the implant into a body lumen. Also attached to the small narrow tube, and placed near the proximal end, is a travel stop, or collar, which prevents the implant from migrating into the body lumen after it has been deployed properly. The small narrow tube is hollow so that a silicone plug, or obturator, can be placed within the hollow portion of the small narrow tube, but which can be removed at a later date to reopen the passage. The proximal end of the implant contains an attachment means that allows the implant to be attached to a delivery catheter during the delivery, and implantation, of the device.

The implant is first affixed onto a delivery catheter which contains a braided tube, which is attached to a handle. A connector means, at the distal end of the braided tube of the delivery catheter, is connected to an attachment means of the implant in order to secure the implant onto the delivery catheter before deployment. The attachment means can be any that is well known in the art, such as a luer connection, a bayonet connection, or a simple screw connection. The braided tube is attached to the handle, which when turned, turns the braided tube, as well as the implant, since it is attached to the braided tube, via the connector, during deployment.

The implant, which is located at the distal end of the braided tube of the delivery catheter, is partly inserted into the entrance of a body lumen, such as the ostium of the fallopian tube. The ostium is reached by first inserting the catheter through the vagina and the cervix of the uterus. After the implant is partly inserted into a body lumen, the handle of the delivery catheter is turned, causing the braided tube, and the attached implant, to rotate. The rotation enables the implant to advance further into the body lumen as the screw threads of the small narrow tube, which are embedded into the wall of the inner lumen of the body lumen, are rotated. The rotation continues until the collar, at the proximal end of the implant, presses against the wall that surrounds the opening of the body lumen. Rotation, as a means to deploy the implant, is favored over devices that are simply pushed into the body lumen, as rotation does not cause axial stress on the body lumen, such as fallopian tubes, which can often lead to complications in the procedure.

After the reversible acute occlusion implant has been positioned within the body lumen, the conical structure, located at the distal end of the implant, is expanded so that the edges of the conical structure press against the wall of the body lumen, providing yet another measure of occlusion for the body lumen. After the conical-shaped structure has been expanded, the handle on the delivery catheter is turned in the opposite direction, so that the connector, located at the distal end of the braided tube of the delivery device, is released from the attachment means at the proximal end on the implant enabling the delivery catheter be withdrawn.

The obturator, which is within the small narrow tube, completely occludes the lumen of the small narrow tube. When it is necessary to reopen the lumen of the small narrow tube, a physician can re-enter the uterus in a similar fashion and pull the obturator out of the implant, hence re-opening the body lumen.

The implant in the present invention can be made of polymeric materials such as silicone, polyurethane, nylon, polyethylene, high density polyethylene or polypropylene, PET, or a combination thereof, or similar material, or biologically derived material, such as a patient's own tissue, or tissue made from stem cells in the form of the above described device. The delivery catheter handle can be made of rigid plastic materials such as ABS or nylon. The braids of the braided tube can be made from nylon with stainless steel wire braiding.

The principle behind the present invention is to provide a means for complete and immediate closure of a body lumen, such as the fallopian tube, eliminating the delay required for tissue growth as a means for occlusion. Immediate closure of a body lumen is achieved via a conical-shaped structure that, when opened into its natural shape, occludes the body lumen by exerting radial pressure on the body lumen's inner wall. The radial force is sufficient enough to generate a hermetic seal. The outer edge of the conical-shaped structure is serrated which enhances the embedment of the outer edge of the conical-shaped structure to the inner wall of the body lumen. The serrations are meant to "cut into" the inner wall of the occluded body lumen. The conical-shaped structure has several struts, which add strength and rigidity, as well as the radial force needed for keeping the conical-shaped structure in the open position, thereby sealing the structure against the inner wall of the body lumen. Additionally, during deployment, the struts make the conical-shaped structure easier to fold against the central tube, where the sheath portions between the struts fold preferentially during folding.

The struts may also contain memory alloys which provide additional radial force, structure, and sealing capabilities of the conical-shaped structure as it presses against the inner wall of the body lumen. The conical structure can be restrained and folded against the implant by wrapping a restraining thread around it using a slip knot. When the implant is positioned within the desired lumen, a retrieval section of the restraining thread extends into the uterus so that it can be pulled via standard surgical equipment thereby releasing the conical structure from its folded position. Then the thread is withdrawn from the patient.

The screw threads of the small narrow tube, which are used to advance the implant into a body lumen as the braided tube of the delivery catheter is rotated, embed into the inner luminal wall of the body lumen, providing an additional measure of occlusion. Additionally, the small narrow tube can include a section within the proximal region that has a larger diameter, providing yet another measure of occlusion to the device. This larger diameter portion will also help prevent the distal and proximal migration of the implanted device.

The device disclosed herein can be used for immediate occlusion of any type of body lumen, especially the fallopian tubes, wherein the device is used to achieve female sterilization. In order to enable complete sterilization, one implant of the present invention is used to occlude each of the fallopian tubes. Several variations of the present inventions are possible. For example, the conical-shaped structure can be placed on the small narrow tube of the implant so that it opens to away from the proximal end of the implanted device or open towards the proximal end of the implanted device. The struts on the conical-shaped structure can be made from shape memory alloy in order to provide sufficient spring action so as to form a seal against the luminal wall of the body lumen. The small narrow tube can be smooth or can be corrugated, the corrugation providing enhanced flexibility and conformity of the device within a body lumen. In addition corrugations help to anchor the inner obturator made from an elastomer like silicone reliably in the implant.

The collar at the proximal end of the device can be made as one circular collar, or can be made as several segments, or lobes, or with shape memory alloys embedded in them, so that the collars will immediately bow outwards once the device is properly positioned via the delivery catheter.

BRIEF DESCRIPTION OF THE DRAWINGS

FIG. 3B depicts the reversible acute occlusion implant of the present invention after it has been deployed within the desired lumen.

FIG. 7 shows the reversible acute occlusion implant attached to the delivery catheter.

DETAILED DESCRIPTION OF THE PREFERRED EMBODIMENT

Figure 1:
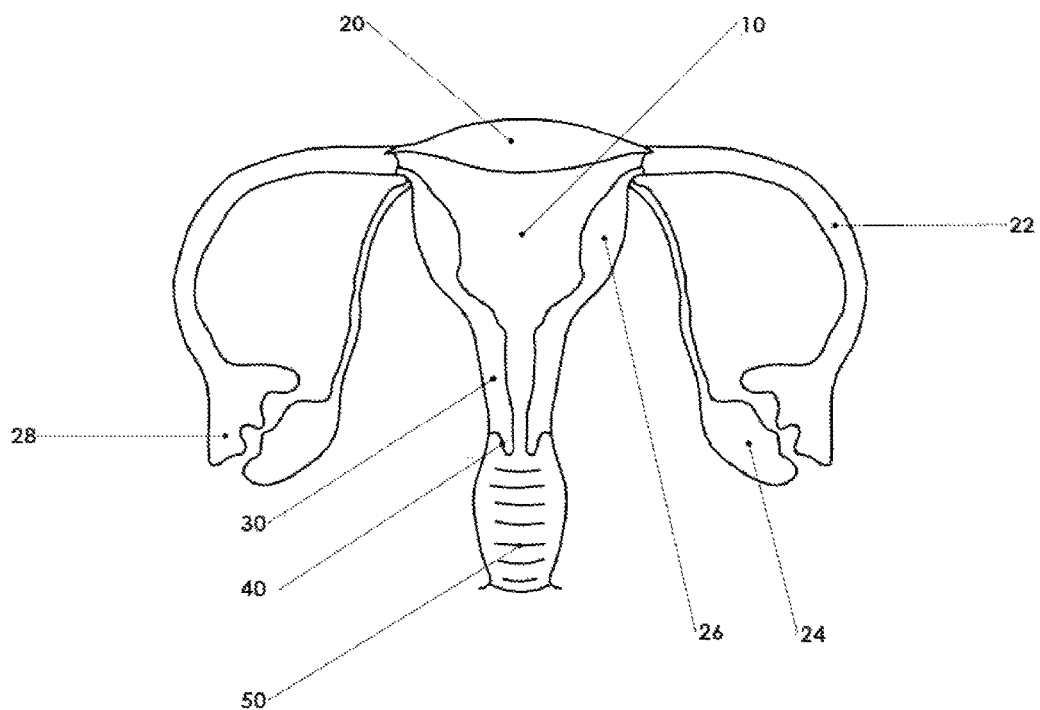
FIG. 1 is a depiction of the human female reproductive system.

FIG. 1 is a diagram of the human female reproductive system. Prior to conception, the ovum, which originates in the overy (24), enters the fimbriae (28), migrates through the fallopian tube (22), and enters the uterus (10) just below the fundus uterus (20). The endometrium (26) is the inner lining of the uterus (10) and the myometrium (30) is just above the cervix (40) which in turn is just above the vagina (50).

Figure 2:
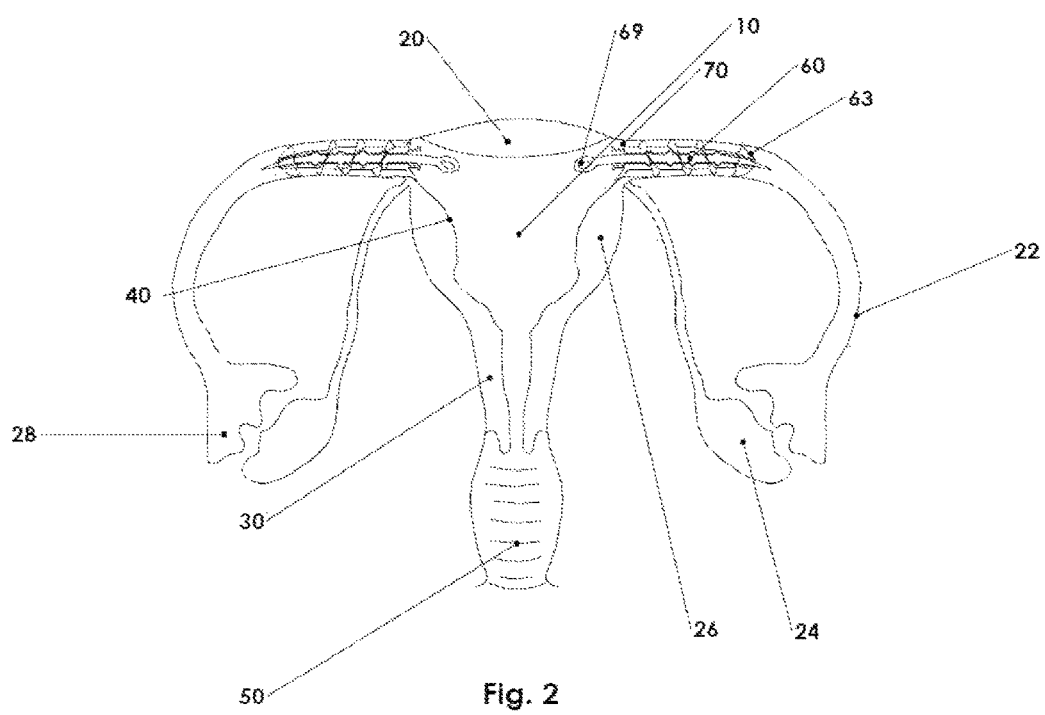
FIG. 2 shows the reversible acute occlusion implant of the present invention after it has been deployed within the fallopian tubes.

FIG. 2 shows the reversible acute occlusion implant (60) of the present invention when it is deployed in the fallopian tubes (22) of the human female. Via a delivery catheter (100 in FIG. 7), the reversible acute occlusion implant (60) is placed into a body lumen, such as the fallopian tube (22). A travel stop, or collar (70), is attached to the proximal end of the reversible acute occlusion implant (60) to prevent the migration of the implant (60) into the body lumen. The distal end of the reversible acute occlusion implant (60) contains a conical structure (63), which when deployed in a body lumen, presses against the inner wall of a body lumen, thereby occluding the body lumen, and preventing the passage of any material or substance through it in either direction.

Figure 3A:
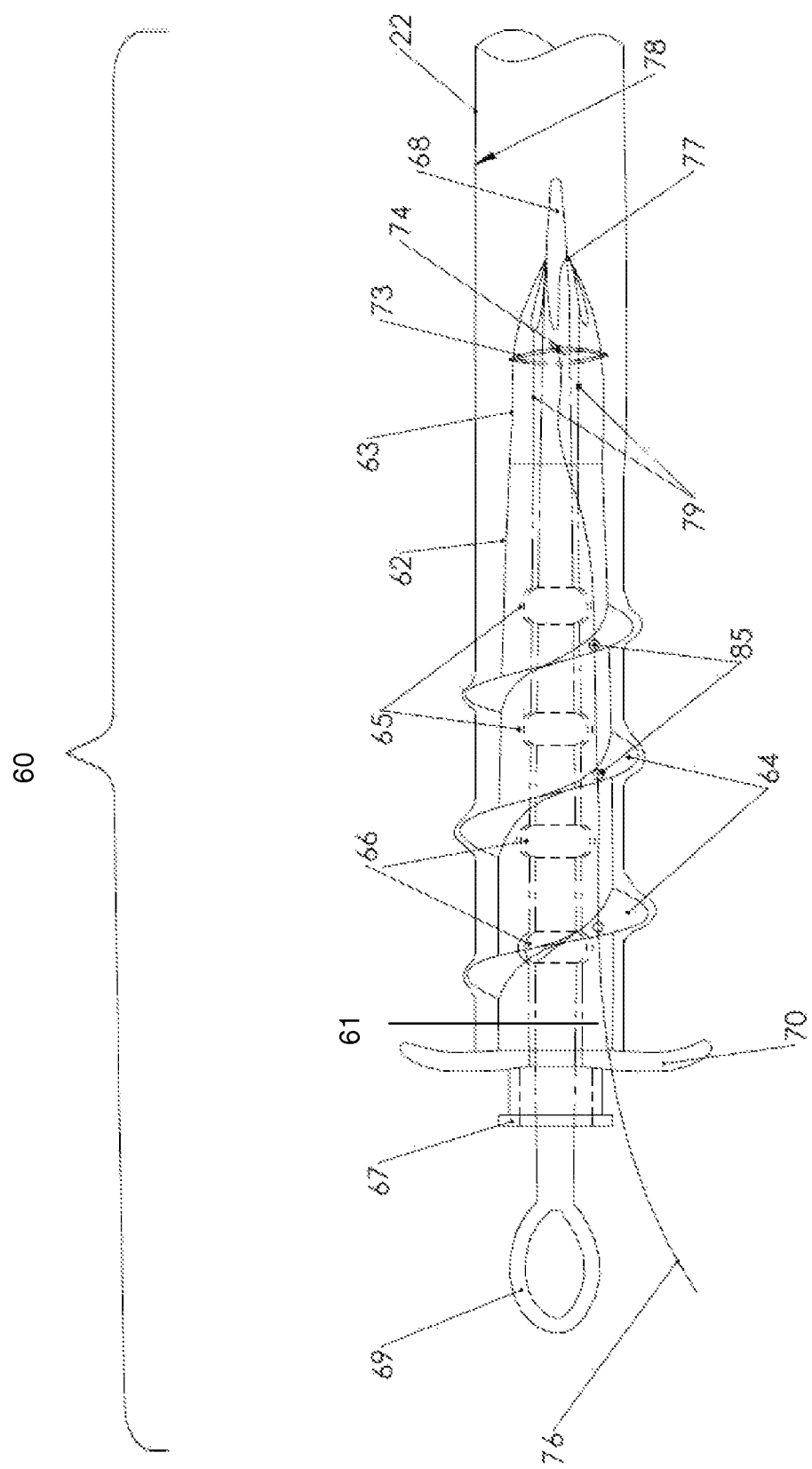
FIG. 3A depicts the reversible acute occlusion implant of the present invention just after implantation, but prior to deployment.

FIG. 3A is the reversible acute occlusion implant (60) of the present invention after it has been inserted into the desired lumen, but before deployment. The reversible acute occlusion implant (60) consists of a small narrow tube (62), with a travel stop, or collar (70), located at the proximal end, and a conical structure (63) at the distal end. The collar (70) prevents the reversible acute occlusion implant (60) from migrating into the body lumen once the reversible acute occlusion implant (60) has been deployed. The small narrow tube (62) of the reversible acute occlusion implant (60) also contains screw threads (64), or serrations, which embed into the inner wall (78) of the body lumen, help to anchor the reversible acute occlusion implant (60) within the body lumen, and provide another measure of occlusion within a body lumen. In its natural, unrestrained state, the conical structure (63) presses against the inner wall (78) of a body lumen, thereby anchoring the reversible acute occlusion implant (60) within a body lumen, and preventing substances from entering or exiting a body lumen. Prior to deployment, the conical structure (63) is restrained, via a restraining thread (73) and slip knot (74), against the outer surface of the reversible acute occlusion implant (60) so that the implant (60) can be properly placed within the lumen ensuring that a retrieval section (76) of the restraining thread (73) extends into the uterus (10). The restraining thread (73) is threaded through a series of aligned holes (85) in the screw threads (64) so that the end, the retrieval section (76), of the restraining thread (73) will extend into the uterus (10). Once the reversible acute occlusion implant (60) is properly positioned within the desired lumen, the retrieval section (76) of the restraining thread (73) is pulled with standard surgical equipment, such as forceps, thereby removing the restraining thread (73) from the conical structure (63) so that the conical structure (63) can (a) return to its natural expanded configuration, with the serrated edge (77) firmly pressing against the inner wall (78) of the body lumen, and (b) facilitate occlusion of the desired body lumen. The conical structure (63) has several struts (79), which add strength and rigidity, as well as the radial force needed for keeping the conical structure (63) in the open position, thereby sealing the structure against the inner wall (78) of the body lumen. The proximal end of the small narrow tube (62) of the reversible acute occlusion implant (60) also contains an attachment means (67) which is used to attach the reversible acute occlusion implant (60) to the braided tubing (110 in FIG. 6A) of a delivery catheter (100 in FIG. 7). A removable obturator (68), or plug, which is composed of silicone, polyurethane, or similar material, fits inside a passage (61) of the small narrow tube (62) of the reversible acute occlusion implant (60) and is held in place within the small narrow tube (62) via a series of corrugations (66) that are positioned along its length, and which, when aligned with corresponding indentations (65) within the inner surface of the small narrow tube (62), lock the removable obturator (68) inside the small narrow tube (62), thereby occluding the small narrow tube (62) and the body lumen. The proximal end of the removable obturator (68) consists of an extraction means, a retrieval loop (69), which, when grasped and pulled with a retrieval catheter (not shown), or similar device, removes the removable obturator (68) from the inside of the small narrow tube (62), thereby opening the small narrow tube (62), reversing the occlusion of the body lumen, and, in the case of the fallopian tube (22), reversing sterilization.

FIG. 3B shows the reversible acute occlusion implant (60) after it has been deployed within a body lumen. Once the restraining thread (73 in FIG. 3A) is removed with standard surgical equipment, such as forceps, the conical structure (63) is released from its folded configuration so that the conical structure (63) can (a) return to its natural expanded configuration, with the serrated edge (77) firmly pressing against the inner wall (78) of the body lumen, and (b) facilitate occlusion of the desired body lumen. The conical structure (63) has several struts (79), which add strength and rigidity, as well as the radial force needed for keeping the conical structure (63) in the open position, thereby sealing the structure against the inner wall (78) of the body lumen.

Figure 4:
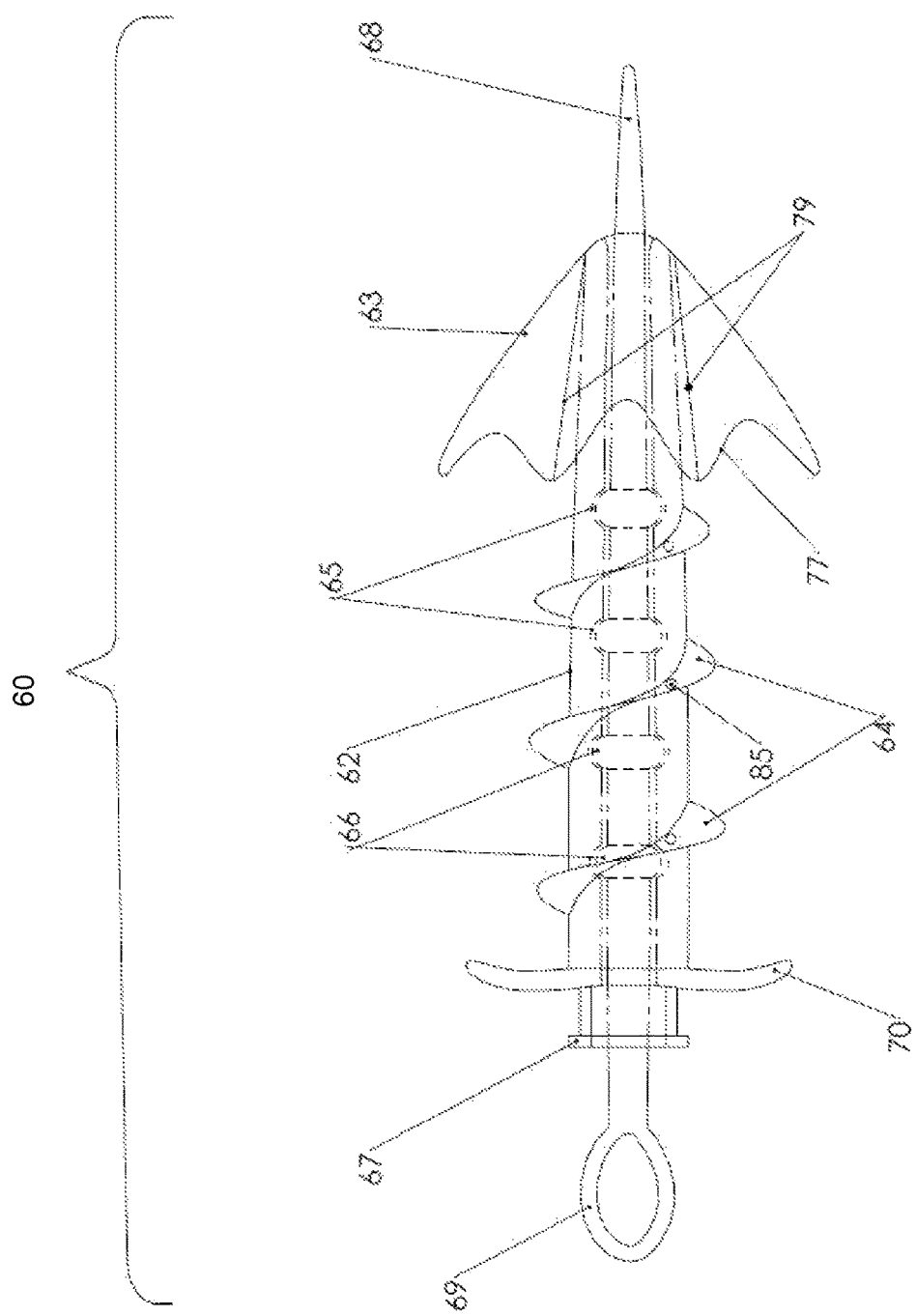
FIG. 4 is another embodiment of the reversible acute occlusion implant.

FIG. 4 is another embodiment of the reversible acute occlusion implant (60). In this embodiment, the conical structure (63), at the distal end of the reversible acute occlusion implant (60), opens proximally.

Figure 5:
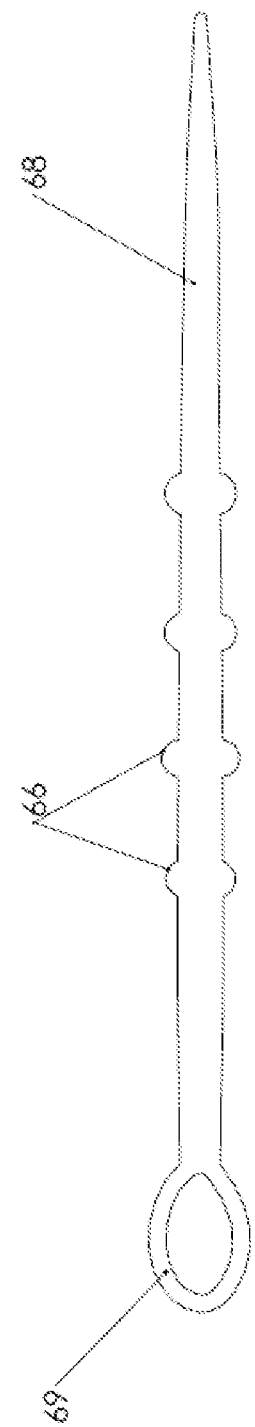
FIG. 5 shows the removable obturator of the present invention.

FIG. 5 is the removable obturator (68) of the reversible acute occlusion implant (60). The removable obturator (68) is placed inside the small narrow tube (62 in FIG. 3A) of the reversible acute occlusion implant (60) before the reversible occlusion device (60) is inserted into the patient. In addition, the removable obturator (68) is locked in place within the small narrow tube (62) when the corrugations (66) of the removable obturator (68) fit into the indentations (65 in FIG. 3A) within the inner surface of the small narrow tube (62 in FIG. 3A). The proximal end of the removable obturator (68) has a retrieval loop (69), which enables the extraction of the removable obturator (68). Once the removable obturator (68) is removed from the small narrow tube (62 in FIG. 3A), the small narrow tube (62 in FIG. 3A) is no longer occluded, so that the patency of, and access of substances through, the body lumen is restored. In the case of the female reproduction system, the removal of the removable obturator (68) reverses the sterilization of the patient because it reverses the occlusion of the fallopian tube (22 in FIG. 1).

Figure 6A:
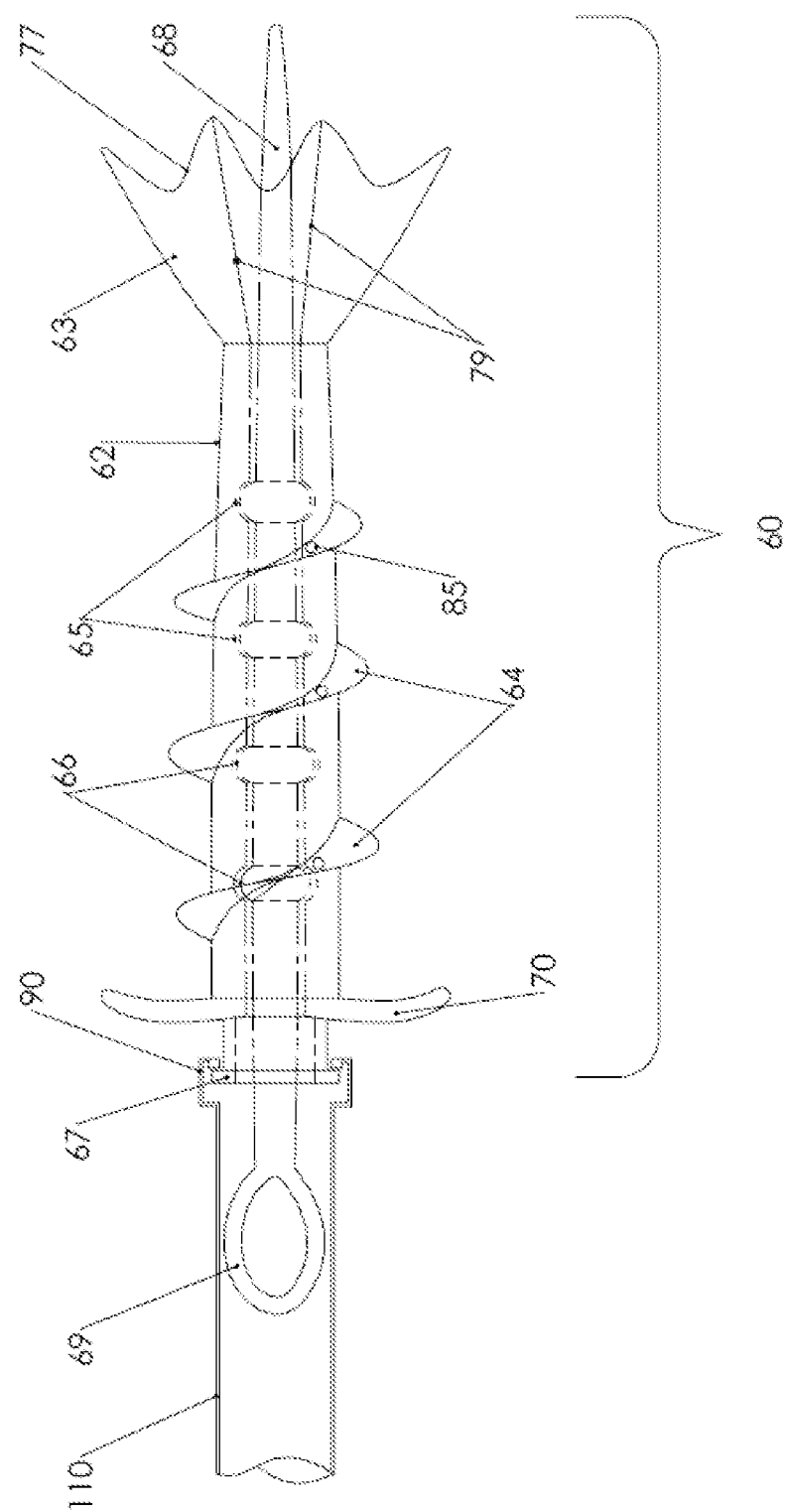
FIG. 6A depicts the reversible acute occlusion implant when it is attached to the braided tubing of the delivery catheter.

FIG. 6A shows the reversible acute occlusion implant (60) when it attached to the braided tubing (110) of the delivery catheter (100 in FIG. 7). The distal end of the braided tubing (110) includes a connector (90) which connects with the attachment means (67) of the reversible acute occlusion implant (60), and which enables the attachment and release of the reversible acute occlusion implant (60) from the delivery catheter (100 in FIG. 7). In this embodiment, the extraction means (69) of the removable obturator (68) fits inside the lumen of the braided tubing (110).

Figure 6B:
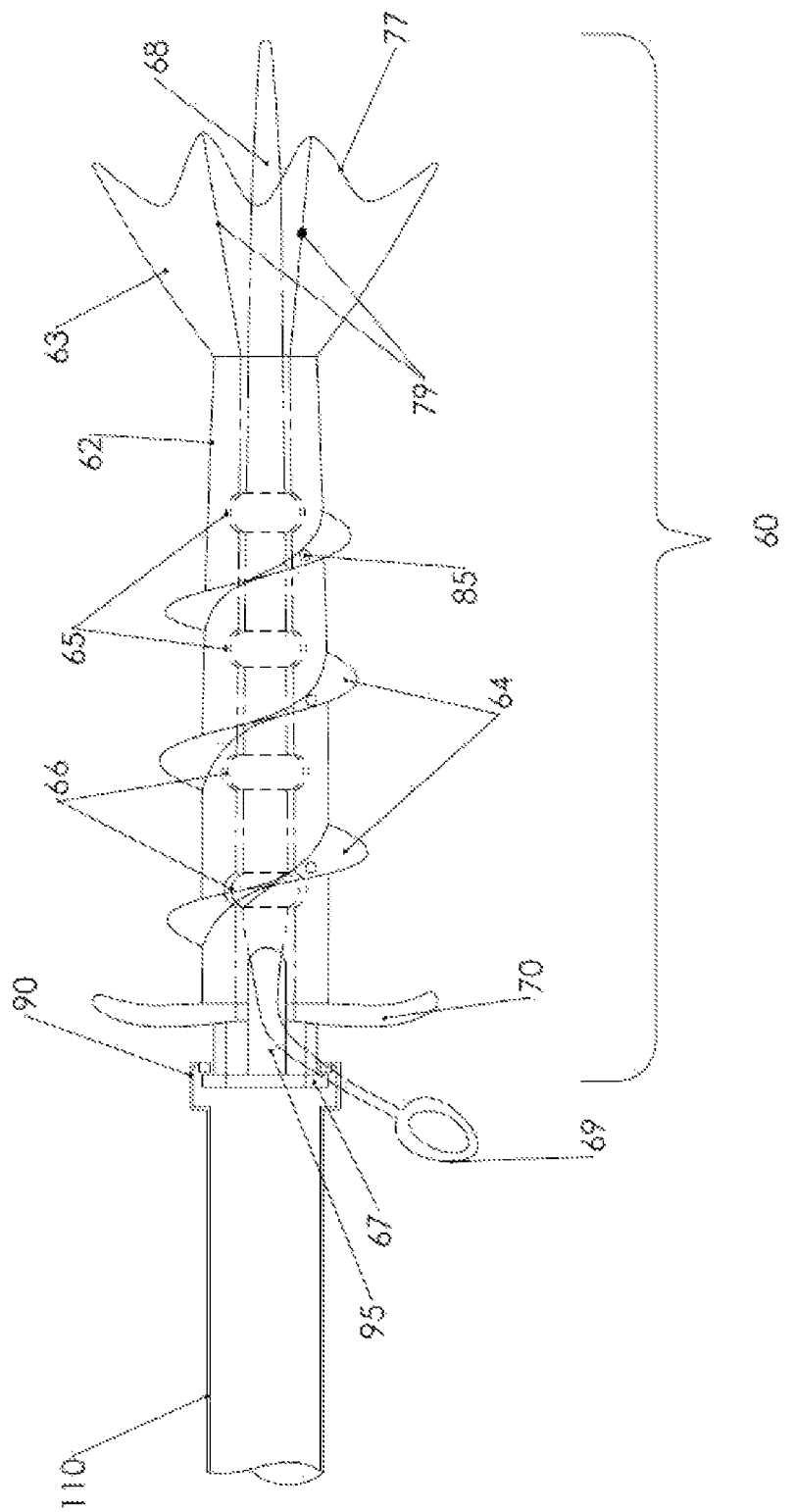
FIG. 6B is another embodiment of the extraction means of the removable obturator.

FIG. 6B shows another embodiment of the extraction means (69) of the reversible acute occlusion implant (60), along with another embodiment of the removable obturator (68), when it is attached to another embodiment of the braided tubing (110) of the delivery catheter (100 in FIG. 7). In this embodiment, the extraction means (69) of the removable obturator (68) extends through a hole (95) in the wall of the proximal end of the small narrow tube (62), instead of extending into the lumen of the braided tubing (110). This embodiment enables the braided tubing (110) to connect directly to the attachment means (67) of the reversible acute occlusion implant (60), and since the extraction means (69) does not extend in the lumen of the braided tubing (110), the braided tubing (110) can have a reduced diameter.

Figure 6C:
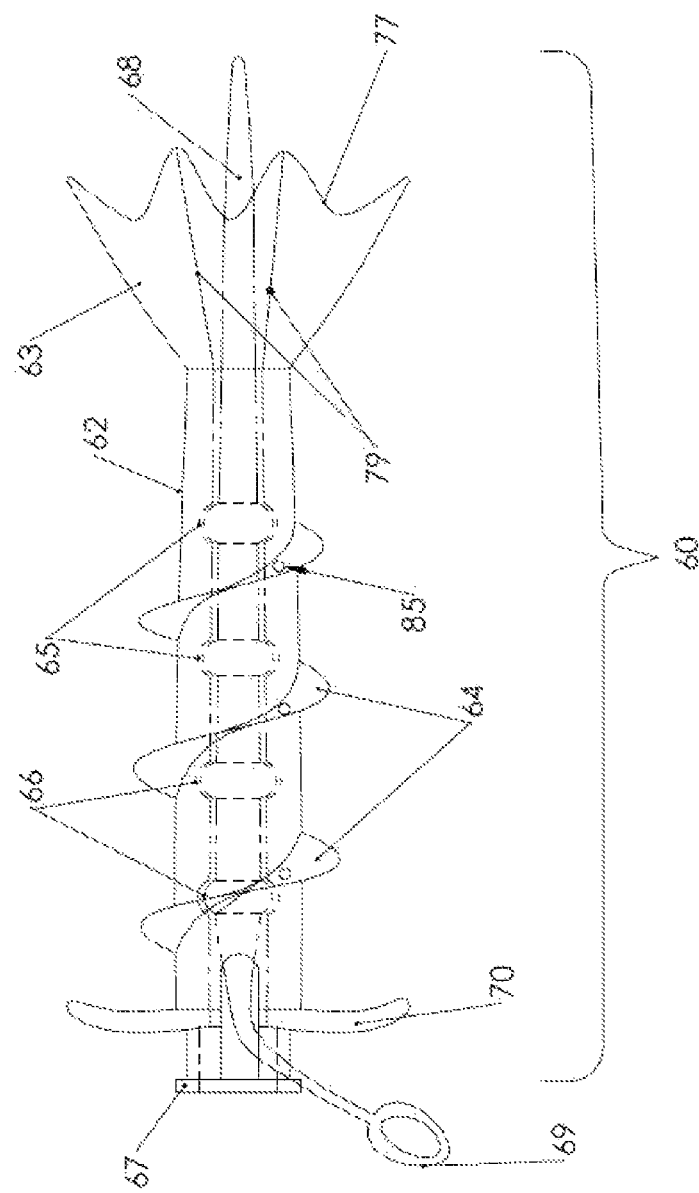
FIG. 6C is the reversible acute occlusion implant as it is being released from the braided tubing of the delivery catheter.
Figure 6C:
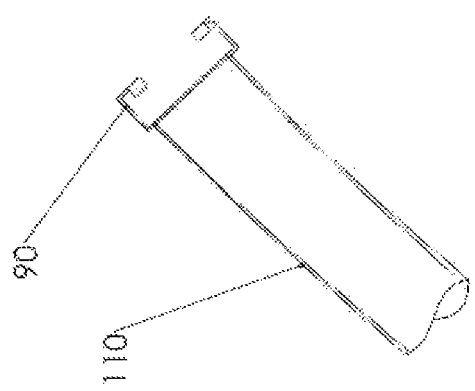

FIG. 6C shows the reversible acute occlusion implant (60) as it is being released from the braided tubing (110) of the delivery catheter (100 in FIG. 7). With the reversible acute occlusion implant (60) attached to the braided tubing (110) of the delivery catheter (100 in FIG. 7), the reversible acute occlusion implant (60) is inserted into the body lumen. Once the reversible acute occlusion implant (60) is properly positioned and secured within the body lumen, the handle (105 in FIG. 7) of the delivery catheter (100 in FIG. 7) is turned, which subsequently rotates the braided tube (110), thereby detaching the attachment means (67) of the reversible acute occlusion implant (60) from the connector (90), and enabling the removal of the delivery catheter (100) from the patient FIG. 7 shows the reversible acute occlusion implant (60) attached to the delivery catheter (100). The delivery catheter (100) has enough rigidity to enable the placement of the reversible acute occlusion implant (60) within the body lumen while also having enough flexibility to migrate through various cavities and vessels of the patient. This dual function is supplied by the braided tubing (110) of the delivery catheter (100). In addition, the braided tubing (110) provides the torque required to detached the connector (90) of the delivery catheter (100) from the attachment means (67) of the reversible acute occlusion implant (60). The torque is delivered to the connector (90) at the distal end of the braided tubing (110) when the handle (105) of the delivery catheter (100) is turned.

We claim:

1. A lumen occluding assembly, comprising:
a hollow body having an open through passage therethrough aligned with a longitudinal axis thereof and a removably mounted obturator in said passage to block flow in said passage and to allow flow through said passage when selectively removed from said passage; a movable occluding device, said movable occluding device having a first end pivotally mounted to an outer surface of said body and an opposite free end configured for selective extension of said free end relative to said first end and away from said longitudinal axis into initial contact with a lumen, said initial contact configured to seal the lumen using a mechanically released stored energy force in said movable occluding device.

2. The assembly of claim 1, wherein:
said movable occluding device selectively remotely operated to occlude the lumen.

3. The assembly of claim 2, wherein:
said occluding device is retained with a retainer mounted to said body.

4. The assembly of claim 3, wherein:
said occluding device is released by a force applied to an elongated releasing member extending through said body.

5. The assembly of claim 3, wherein:
said occluding device is located on said body either proximally or distally of said retainer.

6. The assembly of claim 2, wherein:
said occluding device retains potential energy that is released for said selective occluding of the lumen.

7. A lumen occluding assembly, comprising:
a hollow body having a selectively open passage therethrough aligned with a longitudinal axis thereof;
a movable occluding device, said movable occluding device having a first end pivotally mounted to an outer surface of said body and an opposite free end configured for selective extension of said free end relative to said first end and away from said longitudinal axis into initial contact with a lumen, said initial contact configured to seal the lumen using a mechanically released stored energy force in said movable occluding device;
a removably mounted obturator in said passage to permit subsequent reopening of said passage with said free end in contact with the lumen;
said obturator is releasably locked in said passage.

8. The assembly of claim 7, wherein:
said obturator having an elongated shape and at least one outer surface irregularity for said releasable locking to said passage.

9. The assembly of claim 8, wherein:
said passage having a conforming irregularity to said surface irregularity of said obturator.

10. The assembly of claim 9, wherein:
one of said obturator surface irregularity and said conforming irregularity of said passage comprises at least one projection and the other of said obturator surface irregularity and said conforming irregularity of said passage comprises a at least one depression.

11. The assembly of claim 7, wherein:
said obturator having a loop on a proximal end thereof to facilitate removal.

12. The assembly of claim 7, wherein:
said passage having a lateral opening adjacent a proximal end thereof;
said body having an attachment member at said proximal end;
said obturator extending through said lateral opening.

13. A lumen occluding assembly, comprising:
a hollow body having a passage therethrough;
a movable occluding device mounted to an outer surface of said body;
a removably mounted obturator in said passage;

said movable occluding device selectively remotely operated to occlude the lumen;
said occluding device is retained with a retainer mounted to said body;
said occluding device is released by a force applied to an elongated releasing member extending through said body;
said releasing member comprises a string comprising a slip knot tied around said occluding device.

14. The assembly of claim 13, wherein:
said slip knot releases with a pull force on said string.

15. The assembly of claim 14, further comprising:
a flexible delivery device releasably connected adjacent said open proximal end;
said delivery device comprising a tubular body;
said hollow body is steered through rotation of said tubular body.

16. The assembly of claim 15, wherein:
said delivery device is connected to said hollow body with a pin and slot connection where said slot has at least one bend.

17. The assembly of claim 13, wherein:
said hollow body has a resilient distal end.

18. A lumen occluding assembly, comprising:
a hollow body having a passage therethrough;
a movable occluding device mounted to an outer surface of said body;
a removably mounted obturator in said passage;
said movable occluding device selectively remotely operated to occlude the lumen;
said occluding device comprises a first end secured to said body and a second open end such that a generally open cone shape is defined.

19. The assembly of claim 18, wherein:
said cone shape further comprises at least one axially extending strut.

20. The assembly of claim 19, wherein:
said at least one strut comprises a plurality of circumferentially spaced struts;
said occlusion device folding between adjacent struts when retained by a retainer mounted to said body.

21. The assembly of claim 20, wherein:
at least some of said struts are made of a shape memory alloy to bias said occluding device to sealingly contact the lumen when released by said retainer.

22. The assembly of claim 18, wherein:
said second end further comprises serrations for sealing contact with said lumen.

23. A lumen occluding assembly, comprising:
a hollow body having a passage therethrough;
a movable occluding device mounted to an outer surface of said body;
a removably mounted obturator in said passage;
said passage having a lateral opening adjacent a proximal end thereof;
said body having an attachment member at said proximal end;
said obturator extending through said lateral opening;
said attachment member is selectively engaged by a tubular delivery member having an inside dimension;
said obturator having a loop on a proximal end thereof that is larger than said inside dimension of said delivery member.

24. The assembly of claim 23, wherein:
said tubular delivery member has a braided wall for torque transmission.

25. A lumen occluding assembly, comprising:
a hollow body having a passage therethrough;
a movable occluding device mounted to an outer surface of said body;
a removably mounted obturator in said passage;
said body having an attachment member at said proximal end;
said attachment member is selectively engaged by a tubular delivery member;
said obturator having a loop on a proximal end thereof that is disposed within said tubular delivery member when said tubular delivery member is attached to said attachment member.

26. The assembly of claim 25, wherein:
said tubular delivery member has a braided wall for torque transmission.

27. A lumen occluding assembly, comprising:
a hollow body having a selectively open passage therethrough aligned with a longitudinal axis thereof;
a movable occluding device mounted to an outer surface of said body;
a removably mounted obturator selectively plugging said passage;
said movable occluding device selectively remotely operated and configured for an initial movement into contact with the lumen, said contact sealing the lumen;
said body comprises a helix having a uniform or non-uniform pitch and located on said body and configured to contact the lumen for fixation of said body to the lumen in said pitch defining said helix.

28. The assembly of claim 27, wherein:
said occluding device is released by a force applied to an elongated releasing member extending through openings in flights of said helix.

29. A lumen occluding assembly, comprising:
a hollow body having a passage therethrough;
a movable occluding device mounted to an outer surface of said body;
a removably mounted obturator in said passage;
said movable occluding device selectively remotely operated to occlude the lumen;
said body further comprises a travel stop adjacent a proximal end thereof and on an opposite end of said body from said occluding device.

* * * * *